(12) United States Patent
Levy

(10) Patent No.: US 9,907,586 B2
(45) Date of Patent: Mar. 6, 2018

(54) HUMERAL NAIL HAVING A BRACKET

(71) Applicant: Michael S Levy, Cherry Hill, NJ (US)

(72) Inventor: Michael S Levy, Cherry Hill, NJ (US)

(*) Notice: Subject to any disclaimer, the term of this patent is extended or adjusted under 35 U.S.C. 154(b) by 0 days.

(21) Appl. No.: 15/222,430

(22) Filed: Jul. 28, 2016

(65) Prior Publication Data

US 2018/0028241 A1    Feb. 1, 2018

(51) Int. Cl.
*A61B 17/72* (2006.01)

(52) U.S. Cl.
CPC ................. *A61B 17/7241* (2013.01)

(58) Field of Classification Search
CPC ............ A61B 17/7233; A61B 17/7241; A61B 17/7283; A61B 17/7208; A61B 17/72; A61B 17/744; A61B 17/746
See application file for complete search history.

(56) References Cited

U.S. PATENT DOCUMENTS 5,443,466 A * 8/1995 Shah ..................... A61B 17/72
606/323

FOREIGN PATENT DOCUMENTS

FR    2781360 A1 *  1/2000  ......... A61B 17/7233
FR    2948555 A1 *  2/2011  ......... A61B 17/7233

* cited by examiner

*Primary Examiner* — Julianna N Harvey
(74) *Attorney, Agent, or Firm* — Lauletta Birnbaum LLC

(57) ABSTRACT

A humeral nail device for fixing proximal humerus fractures and rotator cuff tears. The humeral nail device includes a flexible proximal humerus nail adapted to be inserted into a humerus and a fixation bracket attached to the nail adapted to repair soft tissue injuries.

12 Claims, 7 Drawing Sheets

HUMERAL NAIL HAVING A BRACKET

SPONSORED RESEARCH OR DEVELOPMENT

The present invention was not developed with the use of any Federal Funds, but was developed independently by the inventors.

BACKGROUND

1. Field

The present invention relates generally to the field of humeral nail technologies, and more specifically to a humeral nail for fixing proximal humerus fractures and having a bracket for fixing rotator cuff tears.

2. Background

Proximal humeral fractures and rotator cuff tears typically occur together at increasing rates. Age, the mechanism of injury, and dislocations at the time of injury are all risk factors for soft tissue disruption around the bone, such as rotator cuff tears, that may be present with fractures of the humerus in the same region.

There exist devices and techniques that can fix humeral fracture, both proximal ones and fractures in the shaft. There are even ways to fix the soft tissue and hold it in place while bone healing takes place. However, there is currently no intramedullary implant or implant system that can accomplish all of the injury patterns utilizing the same set of implants. Current systems require basically two different surgeries, one to fix the bone and another to fix the soft tissue. This adds time to the case, and it adds additional set ups (sterile cases and increased set up time for the operation). The use of one system/implant can help streamline both the operative time and the operative set up.

As a general surgical rule, any advance either by technique or by implants that can simplify complex suturing techniques and still perform clinically can be a significant advantage. The technique and implants of the present invention can accomplish this by holding the sutures that repair soft tissue to the implant. Fewer holes are needed in the bone to pass the suture through. This reduces the trauma to the already fractured bone. In addition, the use of flexible nails permit smaller incisions. Using an attached bracket also helps reduce the incision, by allowing sutures to be tied and fixed to one central point.

Thus, a need exists for a humeral nail device, that in the same system of implants can provide for humeral fracture proximal fixation, humeral fracture shaft fixation, and soft tissue repair of rotator cuff tears. The nail of the present invention is intended to be employed for fixation of both proximal humeral fractures (around the shoulder), and fractures of the humeral shaft (the tube part of the arm bone). Additionally, the nail can aid in repair of the soft tissue around a proximal humeral fracture (such as a rotator cuff tear). This nail can also be employed when trauma to the shoulder includes both proximal humerus fractures (around the shoulder) and rotator cuff tears. This present invention solves three humeral injury patterns (proximal humeral fractures, humeral shaft fractures, and proximal humeral fractures that also require rotator cuff repairs). The invention includes the combination of at least three unique designs: a flexible nail for fixing proximal humeral fractures, a humeral shaft fracture nail that controls fixation distally without cross locking and an intramedullary nail devices that can also fix rotator cuff tears.

SUMMARY

A humeral nail device for fixing proximal humerus fractures and rotator cuff tears. The humeral nail device includes a flexible proximal humerus nail adapted to be inserted into a humerus and a fixation bracket attached to the nail adapted to repair soft tissue injuries. The flexible nail may comprise an elongated unitary or integral cannulated body having a head portion, a distal tip portion, and an angled frustoconical intermediate body portion that connects the head portion to the distal tip portion. The fixation bracket may comprise a top planar leg and an inclined lateral leg connected thereto, a plurality of suture holes are provided in the lateral leg. A plurality of screw receiving openings may be located along the length of the nail head. And, the nail may be made from a titanium alloy, or stainless steel, or carbon fiber, material.

A connector may be provided between a lower surface of the top leg and an end of the nail head, wherein the nail head is secured to the fixation bracket. The connector may be dovetailed.

BRIEF DESCRIPTION OF THE DRAWINGS

The embodiments will be described in detail with reference to the following drawings in which like reference numerals refer to like elements wherein.

DETAILED DESCRIPTION

FIGS. 1-6 show a humeral nail device 10 for fixing proximal humerus fractures and rotator cuff tears in accordance with a preferred embodiment of the present invention. The nail device 10 includes a flexible proximal humerus nail 12 and an attached fixation bracket 14.

The humeral nail device 10 is intended for metaphyseal (proximal) humeral fractures with or without soft tissue rupture and injury. In addition, the humeral nail device 10 is also intended to be used for diaphysel (shaft) fractures as well.

Figure 1:
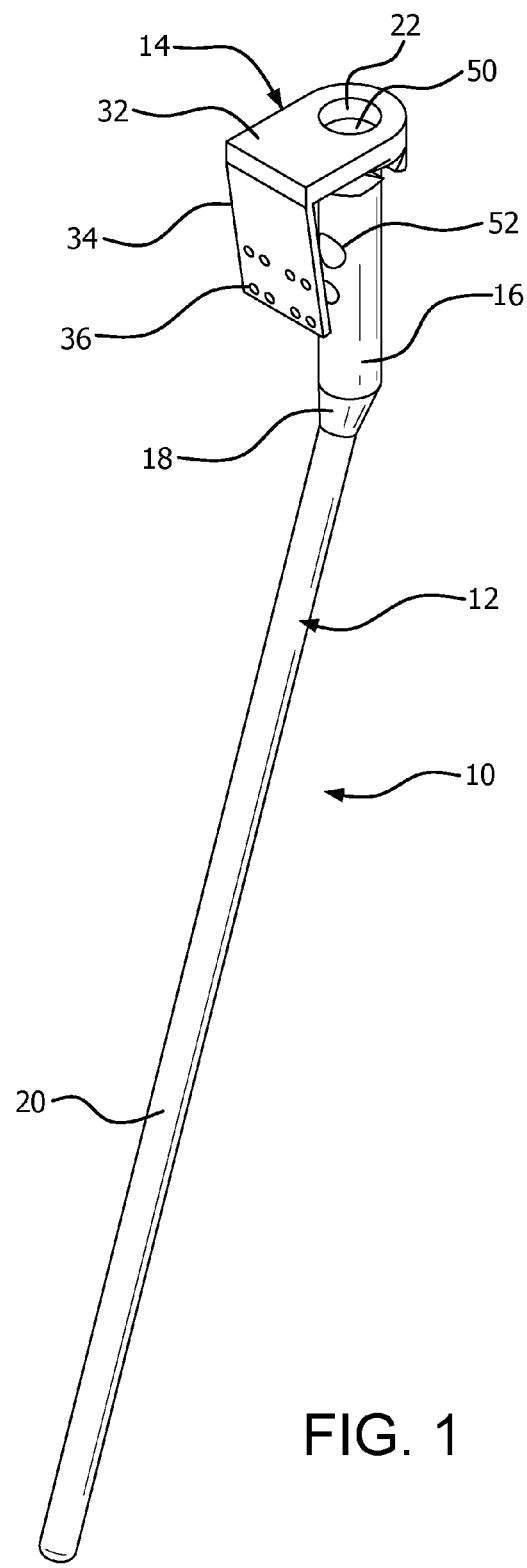
FIG. 1 is a front isometric view of a humeral nail device in accordance with the present invention.
Figure 2:
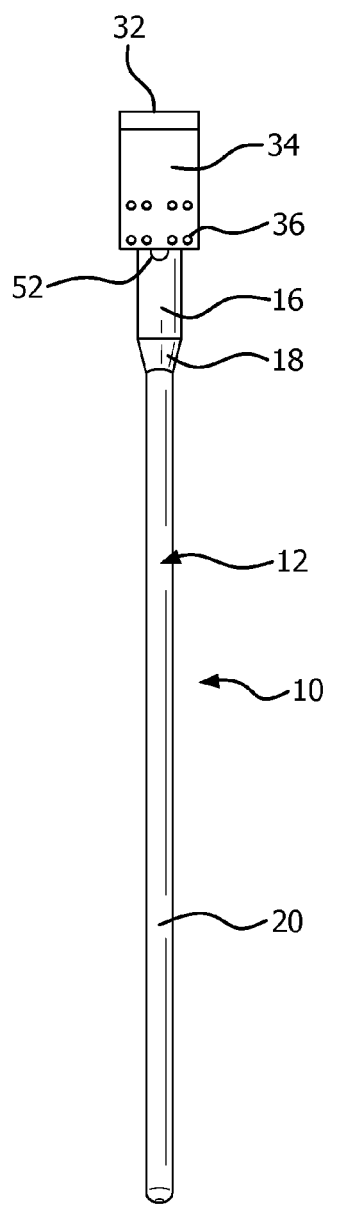
FIG. 2 is a front view of the humeral nail device of FIG. 1.
Figure 3:
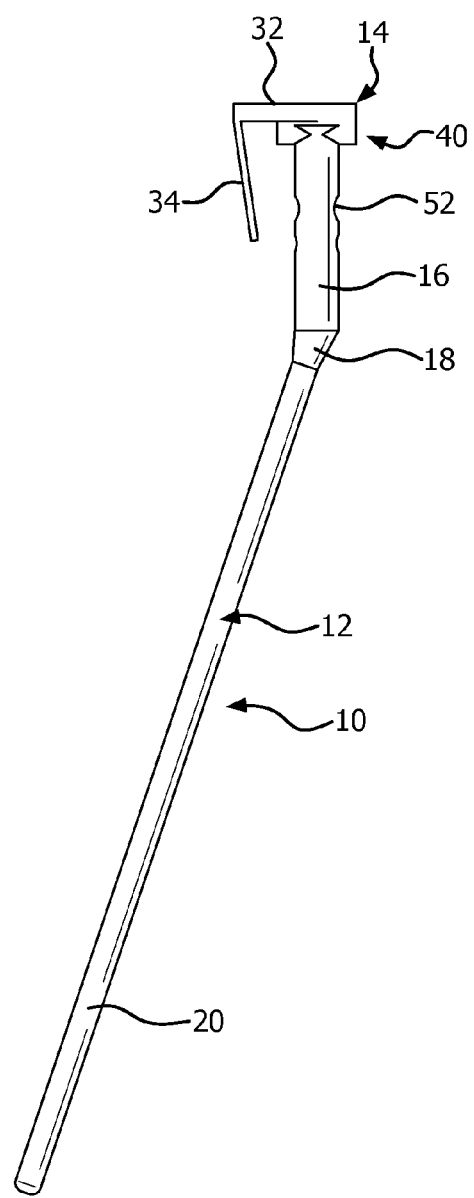
FIG. 3 is a side view of the humeral nail device of FIG. 1.
Figures 4, 5:
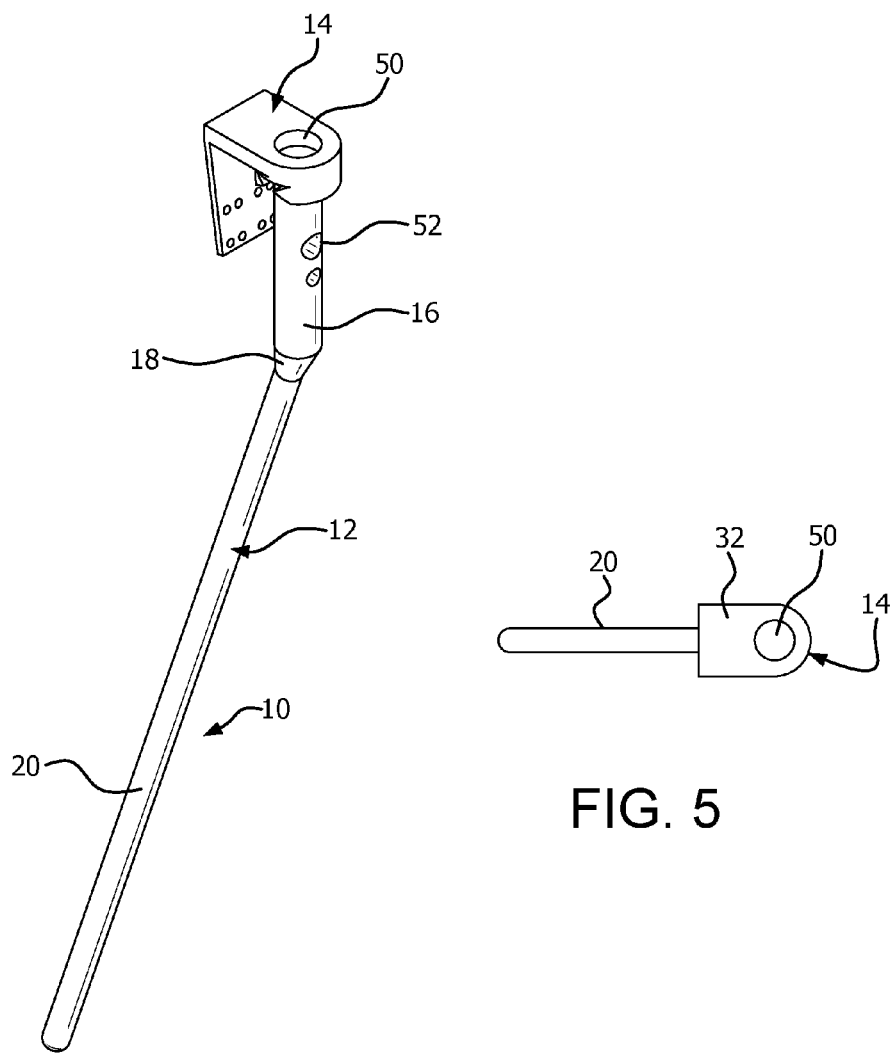
FIG. 4 is a rear isometric view of the humeral nail device of FIG. 1.
FIG. 5 is a top view of the humeral nail device of FIG. 1.
Figure 6:
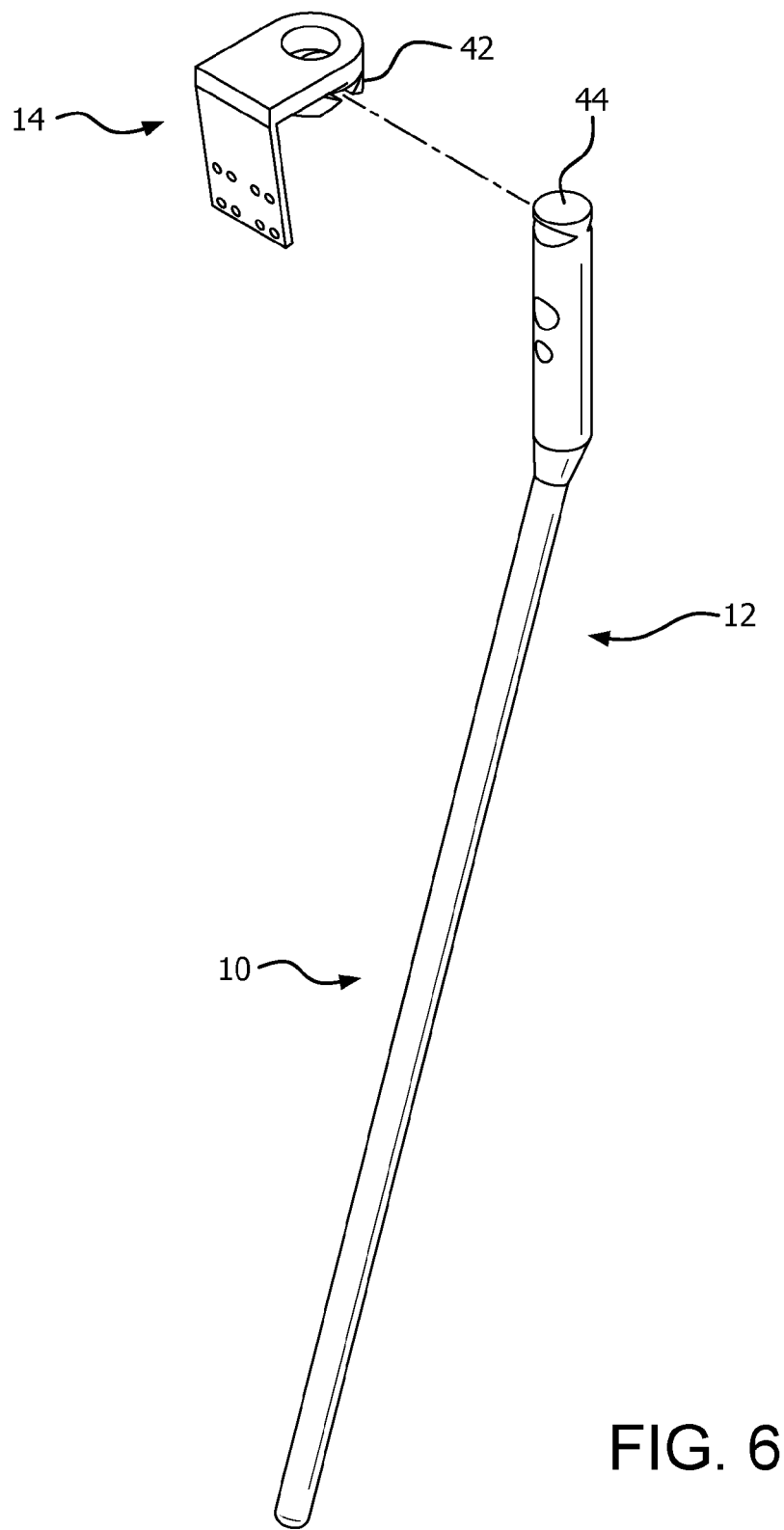
FIG. 6 is an exploded isometric view of the humeral nail device of FIG. 1.
Figure 7:
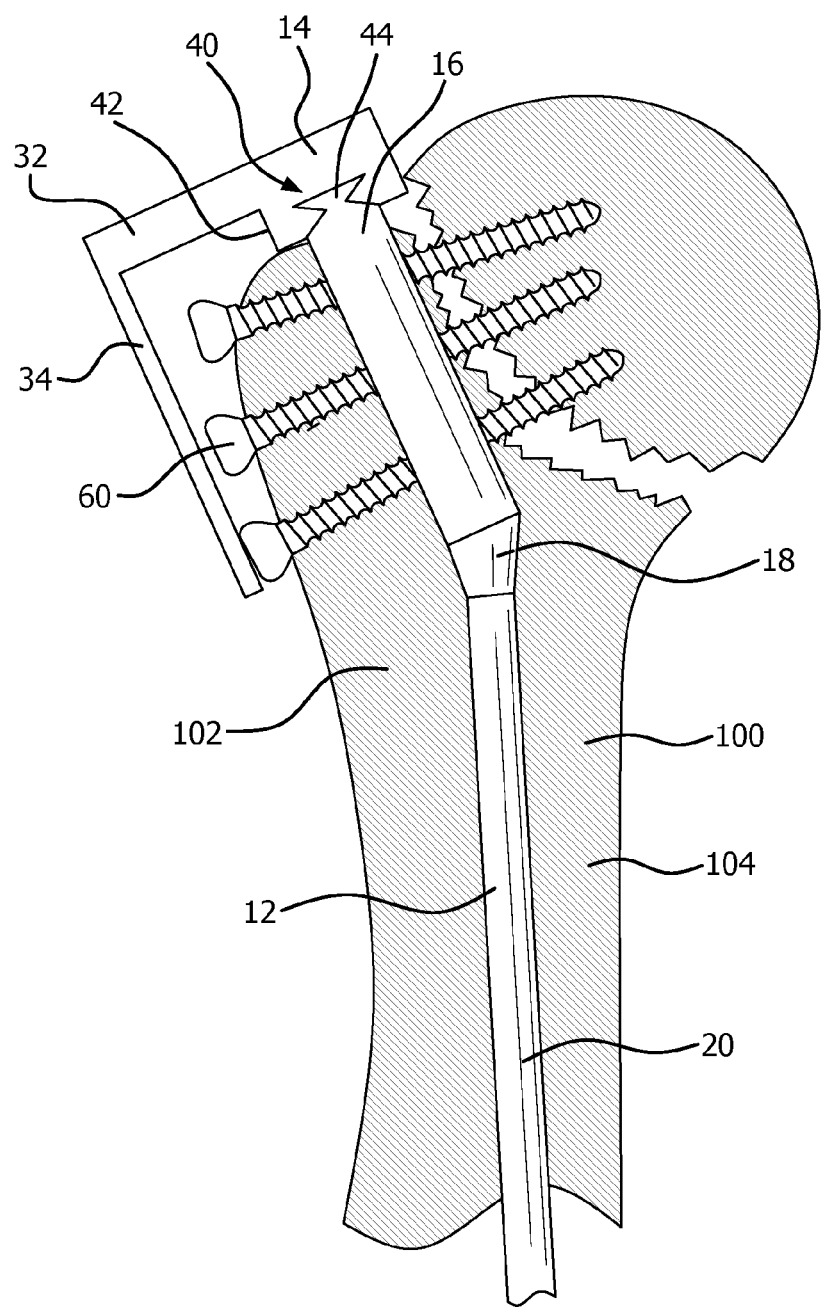
FIG. 7 is a side view of the humeral nail device of FIG. 1 in use.
Figure 8:
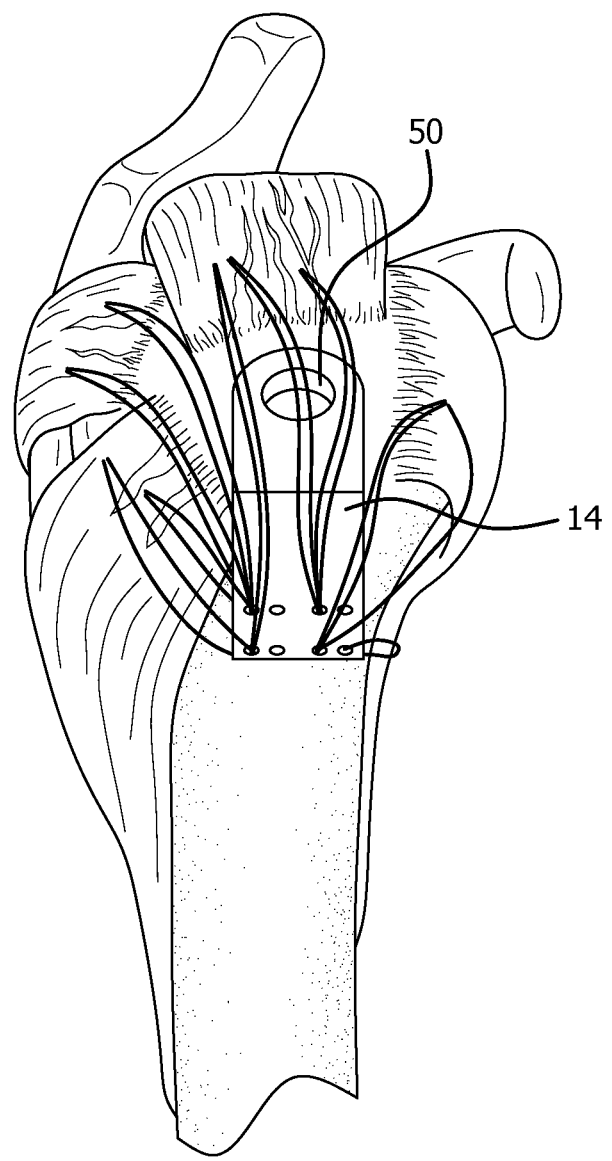
FIG. 8 is a front view of the humeral nail device of FIG. 1 in use.
Figure 9:
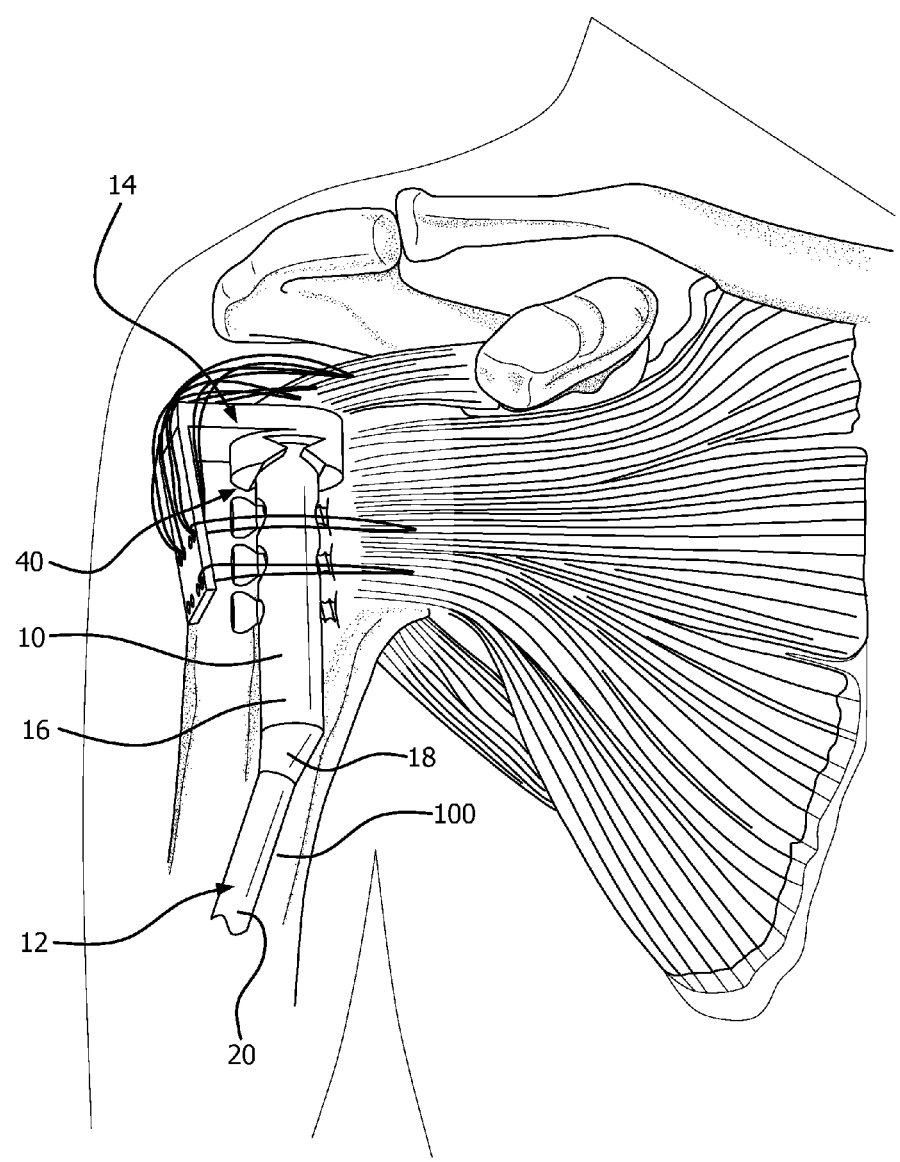
FIG. 9 is a side view of the humeral nail device of FIG. 1 in use.

Referring now to FIGS. 7-9, the humeral nail device 10 device includes a flexible intramedullary nail 12 for insertion into a humerus 100. The nail 12 takes form of an elongated unitary or integral cannulated body having a head 16, an angled frustocontical intermediate body portion 18, and a distal tip portion 20.

As shown in FIGS. 1-7, the nail 12 is inserted into the medullary canal of the humerus 100 to a position in which head 16 is in the proximal region 102 of the humerus 100, and the distal tip 20 is in the distal region 104 of the humerus 100. The head 16 is preferably cannulated or hollow along its length in order to provide an axial opening 22 which extends through the head 16. It is contemplated that the nail 12 be provided in three lengths of from approximately 240 mm to approximately 300 mm. The lengths will cover the sizes necessary to fix most humerus sizes. The nail 12 is inserted into the humerus 100 to a position in which the top end of the head 16 is adjacent to or, preferably, flush with, the entry opening formed in the humerus 100.

The humeral nail device 10 also provides a way to incorporate soft tissue injuries, such as rotator cuff tears into the repair with the use of the fixation bracket 14. The fixation bracket includes a top generally planar leg 32 and an inclined lateral leg 34 connected thereto. A plurality of suture holes 36 are provided in the lateral leg 34 as described in detail below. A connection 40 is provided in the lower surface 36 of the top leg 32 and the end 24 of the nail head 16. The connection preferable takes the form of a partial annulus 42 and a complementary shaped cylindrical tip 44 of the end of the head 16. Preferably, each complementary part 42 and 44 of the connection 40 is dovetailed as shown to secure the bracket 14 to the nail 12. In this way, the fixation bracket 14 can be easily fixed or secured to the top of the nail 12 prior to implantation and that enables soft tissue to be anchored securely to the healing bone.

An opening 50 is also provided through the top leg of the bracket coincident with the connection 40 and the axial opening 22 of the nail 12 which acts as a securing arrangement to secure the head 16 of the nail 12 to a device or a tool used for inserting the nail into the medullar canal. Several screw receiving openings 52 are located along the length of the nail head 16. The holes are 4 mm in diameter to accept cancellous bone screws. The holes are offset 5 degrees from each other. This is a common practice in screw and plate design. Screws that are placed in a straight line may propagate a fracture of worsen an existing fracture. Also offsetting the holes will allow for a wider purchase in the humeral head. The opening to receive screws 60 proximally is threaded and is about 3.5 to about 3.75 mm in diameter. And are adapted to receive the screws 60.

For fractures of the proximal region of the humerus, the medullary canal of the humerus is reamed with an appropriate tool or device according to conventional methods and procedures. The nail is inserted into the canal using conventional methods and appropriate tools and devices, including guiding devices, such as guiding wires. Following the insertion of the nail into the medullary canal, the screws are inserted through the bone and into the openings. For fractures of proximal humerus, the screws are inserted into the proximal openings.

The humeral nail device 10 combines the flexible nail 12 with proximal fixation screws 16. The humeral nail device 10 combines ease of insertion without the need for distally cross locking.

The flexibility of the nail 12 permits the nail 12 to become settled distally in the humerus 100. One preferred material to provide the requisite strength and flexibility is a titanium alloy, which would add to the flexibility of the nail. The proximal fixation implant 10 also provides a way to incorporate soft tissue injuries, such as rotator cuff tears into the repair with the use of the fixation tab 14. The fixation tab 14 can be easily fixed or secured to the top of the nail 12 prior to implantation and that enables soft tissue to be anchored securely to the healing bone.

The screws 16 are inserted through the nail 12 in the proximal portion with the aid of a targeting guide (not shown) and provide proximal fixation.

The nail 12 is an intramedullary device for humeral fractures. It is typically placed thru a small incision just above the top lateral corner of the humerus 100, using either an awl (not shown) or placed directly through an existing fracture fragment. An insertion tool (not shown) is used to place the nail 12 into the humerus 100 and helps guide the nail 12 into place.

The length of the nail 12 is chosen by the surgeon and is determined prior to surgery. The 12 nail is seated into the distal humerus either by hand or with the use of a mallet.

This nail system treats proximal humerus fractures (close to the shoulder joint), fractures in the shaft of the humerus, and proximal humeral fractures that also have soft tissue injuries such as a rotator cuff tear.

The nail 12 fixes a proximal humeral fracture with cross locking screws 60. The screws 60 are inserted with the use of an external guide. The screws 60 pass through the nail 12 and hold the fracture fragments together. The screws 60 are oriented at different angles, to improve the holding power in weak bone.

Typically, the nail 12 locks only proximally. Length and rotational control is maintained by driving the nail into distal metaphyseal bone (by the elbow). Also the nail 12 can be inserted into the intramedullary canal of the humerus without reaming the diaphysel bone. If there is no additional step of reaming the canal, surgical time is reduced.

Although embodiments have been described with reference to a number of illustrative embodiments thereof, it should be understood that numerous other modifications and embodiments can be devised by those skilled in the art that will fall within the spirit and scope of the principles of this disclosure. More particularly, various variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

What is claimed is:

1. A humeral nail device for fixing proximal humerus fractures and rotator cuff tears, comprising a flexible proximal humerus nail configured to be inserted into a humerus, the flexible nail comprising an elongated unitary or integral body having a cylindrical head portion configured to be inserted into the medullary canal of the humerus and sized such that the head portion is adjacent an entry opening in the humerus when so inserted, a distal tip portion, and an angled frustoconical intermediate body portion that connects the head portion to the distal tip portion such that the distal tip portion is at an acute angle relative to a centerline of the head portion, and a fixation bracket attached to the nail configured to enable soft tissue to be anchored securely to the humerus, the fixation bracket comprising a top planar leg plate and an inclined lateral planar leg plate connected thereto and extending at an acute inclined angle relative to the top leg plate back towards the head portion, a plurality of suture holes are provided in the lateral leg sized to accommodate a suture therein to secure the soft tissue.

2. The humeral nail device in accordance with claim 1 wherein a connector is provided between a lower surface of the top leg and a proximal end of a head portion of the nail such that the lower surface of the top leg abuts the proximal end of the head portion, the proximal end extending along a longitudinal centerline of the head portion, wherein the head portion is secured to the fixation bracket.

3. The humeral nail device in accordance with claim 2 wherein the connector is a circular dovetailed connection.

4. The humeral nail device in accordance with claim 1 wherein a plurality of screw receiving openings are located along the length of the head portion, and are positioned to be adjacent the metaphyseal portion of the humerus to secure the screws into the metaphyseal portion in use.

5. The humeral nail device in accordance with claim 1 wherein the nail is made from a titanium alloy material.

6. A humeral nail device to fix proximal humerus fractures and rotator cuff tears, comprising
   a flexible intramedullary humerus nail adapted to be inserted into a medullary canal of a humerus, the nail having an elongated cylindrical distal tip body and a proximal head portion having a cylindrical shape, a longitudinal axis of the elongated body being at an acute angle relative to a longitudinal axis of the head portion, the elongated body being sized such that a top of the head portion is substantially flush with an entry opening in the humerus when the nail is inserted into the medullary canal during use, and
   a fixation bracket attached via a connector to the head portion, the bracket having rows of holes having a diameter substantially the same size as a diameter of a suture and sized to accept sutures therein to enable soft tissue to be anchored securely to the humerus during use, the fixation bracket having a top plate and a lateral plate extending therefrom at an acute angle back towards the elongated body of the nail, the connector having a first part extending outwardly from the top of the head portion and coaxially along the longitudinal axis of the head portion, and a complementary second part formed in the top plate.

7. The humeral nail device in accordance with claim 6 wherein one of the first and second parts being a partial annulus and the other of the first and second parts being a complementary extending tip.

8. The humeral nail device in accordance with claim 7 wherein the connector being a circular dovetailed connection.

9. The humeral nail device in accordance with claim 7 wherein the nail has a frustoconical intermediate portion connecting the distal tip body and the head portion, a longitudinal axis of the intermediate portion being coincident with the longitudinal axis of the distal tip body.

10. The humeral nail device in accordance with claim 9 wherein a plurality of screw receiving openings are located along the length of the head portion, the screw opening being offset by 5 degrees from each other, the screw openings are positioned to be adjacent an epiphyseal portion of the humerus to secure screws into the epiphyseal portion.

11. The humeral nail device in accordance with claim 10 wherein the top plate has a tool opening coincident with the connector opening to receive an insertion tool therein.

12. The humeral nail device in accordance with claim 11 wherein the nail having a length between 240 mm and 300 mm and the nail is made from a titanium alloy material.

* * * * *